(12) United States Patent
Moore et al.

(10) Patent No.: US 7,109,004 B2
(45) Date of Patent: Sep. 19, 2006

(54) PROCESS FOR REDUCING AN ALPHA-KETO ESTER

(75) Inventors: Jeffrey C. Moore, Westfield, NJ (US); Michael G. Sturr, Mountainside, NJ (US); Kathleen McLaughlin, Edison, NJ (US); Jaehon Kim, Fort Lee, NJ (US)

(73) Assignee: Merck & Co., Inc., Rahway, NJ (US)

( * ) Notice: Subject to any disclaimer, the term of this patent is extended or adjusted under 35 U.S.C. 154(b) by 559 days.

(21) Appl. No.: 10/616,320

(22) Filed: Jul. 8, 2003

(65) Prior Publication Data

US 2004/0101937 A1    May 27, 2004

Related U.S. Application Data

(60) Provisional application No. 60/394,761, filed on Jul. 10, 2002.

(51) Int. Cl.
*C12P 7/42* (2006.01)
*C12P 7/60* (2006.01)
*C12P 7/62* (2006.01)
*C12N 9/02* (2006.01)

(52) U.S. Cl. ............. 435/146; 435/135; 435/138; 435/189

(58) Field of Classification Search ............. 435/135, 435/138, 139, 146, 189
See application file for complete search history.

(56) References Cited

U.S. PATENT DOCUMENTS 5,371,014 A * 12/1994 Matsuyama et al. ........ 435/280

OTHER PUBLICATIONS

Michihiko Kataoka, et al., Biochimica et Biophysica Acta, 1122 (1992) 57-62.
Michihiko Kataoka, et al., Arch Microbiol, (1992) 157:279-283.
Keiko Kita, et al., Applied and Environmental Microbiology, Jul. 1996, p. 2303-2310.
G. Krix, et al., Journal of Biotechnology, 53, (1997) 29-39.
Anita Schummer, et al., Tetrahedron, vol. 47, No. 43, pp. 9019-9034, 1991.
Sakayu Shimizu, et al., Journal of Molecular Catalysis B: Enzymatic 5 (1998) 321-325.
Sakayu Shimizu, et al., Applied and Environmental Microbiology, Aug. 1990, p. 2374-2377.
H. Simon, Pure & Appl. Chem., vol. 64, No. 8, pp. 1181-1186, 1992.

* cited by examiner

*Primary Examiner*—Jean C. Witz
*Assistant Examiner*—Susan Hanley
(74) *Attorney, Agent, or Firm*—Richard S. Parr; Valerie J. Camara

(57) ABSTRACT

A process for preparing (R)-hydroxy ester (II)

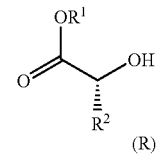

from alpha-keto ester I

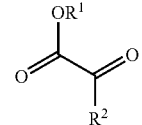

comprising adding the alpha-keto ester I to a mixture comprising the ketoreductase enzyme and non-ketoreductase enzyme components, wherein the ketoreductase enzyme has a molecular weight between 36000 and 38000, and wherein the ketoreductase enzyme has an N-terminal amino acid sequence selected from the group of sequences consisting of (SEQ. ID NO. 1)
Ala-Ile-Pro-Asp-Asn-Ala-Val-Leu-Glu-Gly-Ser-Leu-Val-Lys-Val-Thr-Gly-Ala-Asn-Gly (SEQ. ID NO. 4)
Met-Ala-Ile-Pro-Asp-Asn-Ala-Val-Leu-Glu-Gly-Ser-Leu-Val-Lys-Val-Thr-Gly-Ala-Asn-Gly, and (SEQ. ID NO. 2)
Met-Ala-Lys-Ile-Asp-Asn-Ala-Val-Leu-Pro-Glu-Gly-Ser-Leu-Val-Leu-Val-Thr-Gly-Ala-Asn-Gly.

7 Claims, No Drawings

SEQUENCE LISTING

<160> NUMBER OF SEQ ID NOS: 4

<210> SEQ ID NO 1
<211> LENGTH: 20
<212> TYPE: PRT
<213> ORGANISM: Artificial Sequence
<220> FEATURE:
<223> OTHER INFORMATION: PRIMER

```
-continued

<400> SEQUENCE: 1

Ala Ile Pro Asp Asn Ala Val Leu Glu Gly Ser Leu Val Lys Val Thr
 1               5                  10                  15

Gly Ala Asn Gly
            20

<210> SEQ ID NO 2
<211> LENGTH: 22
<212> TYPE: PRT
<213> ORGANISM: SPOROBOLOMYCES SALMONICOLOR

<400> SEQUENCE: 2

Met Ala Lys Ile Asp Asn Ala Val Leu Pro Glu Gly Ser Leu Val Leu
 1               5                  10                  15

Val Thr Gly Ala Asn Gly
            20

<210> SEQ ID NO 3
<211> LENGTH: 343
<212> TYPE: PRT
<213> ORGANISM: SPOROBOLOMYCES SALMONICOLOR

<400> SEQUENCE: 3

Met Ala Lys Ile Asp Asn Ala Val Leu Pro Glu Gly Ser Leu Val Leu
 1               5                  10                  15

Val Thr Gly Ala Asn Gly Phe Val Ala Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Val Ser
                85                  90                  95

Phe Ser Asn Lys Tyr Asp Glu Val Thr Pro Ala Ile Gly Gly Thr
            100                 105                 110

Leu Asn Ala Leu Arg Ala Ala Ala Thr Pro Ser Val Lys Arg Phe
        115                 120                 125

Val Leu Thr Ser Ser Thr Val Ser Ala Leu Ile Pro Lys Pro Asn Val
130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Asn Tyr
        195                 200                 205

Thr Ile Gly Thr Ile Phe Asp Pro Glu Thr Gln Ser Gly Ser Thr Ser
    210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Arg Val Tyr
```

```
                  260                 265                 270
Gly Thr Ala Gly Thr Phe Asp Trp Asn Thr Val Leu Ala Thr Phe Arg
            275                 280                 285
Lys Leu Tyr Pro Ser Lys Thr Phe Pro Ala Asp Phe Pro Asp Gln Gly
            290                 295                 300
Gln Asp Leu Ser Lys Phe Asp Thr Ala Pro Ser Leu Glu Ile Leu Lys
305                 310                 315                 320
Ser Leu Gly Arg Pro Gly Trp Arg Ser Ile Glu Glu Ser Ile Lys Asp
                325                 330                 335
Leu Val Gly Ser Glu Thr Ala
            340

<210> SEQ ID NO 4
<211> LENGTH: 21
<212> TYPE: PRT
<213> ORGANISM: Artificial Sequence
<220> FEATURE:
<223> OTHER INFORMATION: PRIMER

<400> SEQUENCE: 4

Met Ala Ile Pro Asp Asn Ala Val Leu Glu Gly Ser Leu Val Lys Val
 1               5                  10                  15
Thr Gly Ala Asn Gly
            20
```

PROCESS FOR REDUCING AN ALPHA-KETO ESTER

This application claims the benefit of Provisional application Ser. No. 60/394,761, filed Jul. 10, 2002.

BACKGROUND OF THE INVENTION

The invention is a process for providing high yields of an (R)-hydroxy ester by reducing an alpha-keto ester using a ketoreductase enzyme.

Simon et al., Pure & Appl. Chem., Vol. 64, No. 8, pp. 1181–1186, 1992, describes properties and mechanistic aspects of redox enzymes from anaerobes suitable for bioconversions. Kataoka et al., Biochimica et Biophysica Acta 1122 (1992) 57–62, describes an NADPH-dependent aldehyde reductase (EC 1.1.1.2) isolated from red yeast *Sporobolomyces salmonicolor* AKU 4429, which catalyzes the reductions of D-glucuronate, D-glucose, D-xylose and D-galactose at high concentrations. Kataoka et al., Arch. Microbial. (1992) 157: 279–283, describes distribution and immunological characterization of microbial aldehyde reductases in red yeast *Sporobolomyces salmonicolor* AKU 4429. Kita et al., Applied and Environmental Microbiology, July 1996, p. 2303–2310, describe cloning of aldehyde reductase gene from red yeast *Sporobolomyces salmonicolor* AKU 4429, and characterization of the gene and its product.

Yasohara et al., Appl. Microbiol. Biotechnol. (1999) 51: 847–851, describe synthesis of optically active ethyl 4-chloro-3-hydroxybutanoate by microbial reduction using *Candida magnoliae*. Shimizu et al., Journal of Molecular Catalysis B: Enzymatic 5 (1998) 321–325, describes chiral alcohol synthesis with *Sporobolomyces salmonicolor* and *Candida magnoliae* yeast carbonyl reductases. Shimizu et al. Applied and Environmental Microbiology, August 1990 p. 2374–2377, describes stereoselective reduction of ethyl 4-chloro-3-oxobutanoate by a microbial aldehyde reductase in an organic solvent-water diphasic system. Aldehyde reductase isolated from *Sporobolomyces salmonicolor* AKU 4429 and glucose dehydrogenase were used. Krix et al. Journal of Biotechnology 53 (1997) 29–39 describe enzymatic reduction of alpha-keto acids leading to L-amino acids, D- or L-hydroxy acids. The investigation used leucine dehydrogenase and phenylalanine dehydrogenase isolated from different organisms.

Schummer et al., Tetrahedron Vol. 47, No. 43, pp. 9019–9034, 1991, describes polyfunctional (R)-2-hydroxycarboxylic acids by reduction of 2-oxo acids with hydrogen gas or formate and resting cells of *Proteus vulgaris.*

SUMMARY OF THE INVENTION

The invention is a process for preparing (R)-hydroxy esters from alpha-keto esters, using an enzymatic reduction step for reducing the alpha-keto ester to the corresponding (R)-hydroxy ester. The (R)-hydroxy ester can be hydrolyzed to form the corresponding (R)-hydroxy acid, which is ultimately useful for making pharmaceutical compounds such as thrombin inhibitors.

DETAILED DESCRIPTION OF THE INVENTION

In the process, the alpha-keto ester I

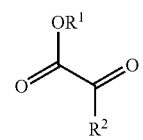

is reduced to (R)-hydroxy ester (II)

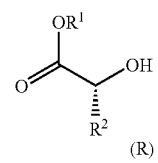

wherein
$R^1$ is $C_{1-4}$ alkyl; and
$R^2$ is selected from the group consisting of
  $C_{1-8}$ alkyl,
  $C_{1-8}$ alkyl, substituted with $C_{3-7}$ cycloalkyl,
  aryl, and
  a 5- to 7-membered saturated or unsaturated heterocyclic ring.

The reduction is induced with a ketoreductase enzyme having a molecular weight between 36000 and 38000, and having an N-terminal amino acid sequence selected from the group of sequences consisting of

```
Ala-Ile-Pro-Asp-Asn-Ala-Val-Leu-Glu-Gly-Ser-Leu-Val-Lys-Val-    (SEQ. ID NO. 1)
Thr-Gly-Ala-Asn-Gly,

Met-Ala-Ile-Pro-Asp-Asn-Ala-Val-Leu-Glu-Gly-Ser-Leu-Val-Lys-    (SEQ. ID NO. 4)
Val-Thr-Gly-Ala-Asn-Gly, and Met-Ala-Lys-Ile-Asp-Asn-Ala-Val-Leu-Pro-Glu-Gly-Ser-Leu-Val-    (SEQ ID NO. 2)
Leu-Val-Thr-Gly-Ala-Asn-Gly.
```

A ketoreductase enzyme having a molecular weight between 36000 and 38000, and having the N-terminal amino acid sequence Met-Ala-Ile-Pro-Asp-Asn-Ala-Val-Leu-Glu-Gly-Ser-Leu-Val-Lys-Val-Thr-Gly-Ala-Asn-Gly (SEQ ID NO. 4), is commercially available as Ketoreductase 1001 (KRED-1001) from BioCatalytics, Inc. (Pasadena, Calif.).

A ketoreductase enzyme having a molecular weight between 36000 and 38000, and having the N-terminal amino acid sequence Met-Ala-Lys-Ile-Asp-Asn-Ala-Val-Leu-Pro-Glu-Gly-Ser-Leu-Val-Leu-Val-Thr-Gly-Ala-Asn-Gly (SEQ ID NO. 2), has the complete sequence

```
Met-Ala-Lys-Ile-Asp-Asn-Ala-Val-Leu-Pro-Glu-Gly-Ser-Leu-Val-Leu-Val-Thr-Gly-     (SEQ ID NO. 3)

Ala-Asn-Gly-Phe-Val-Ala-Ser-His-Val-Val-Glu-Gln-Leu-Leu-Glu-His-Gly-Tyr-Lys-

Val-Arg-Gly-Thr-Ala-Arg-Ser-Ala-Ser-Lys-Leu-Ala-Asn-Leu-Gln-Lys-Arg-Trp-Asp-

Ala-Lys-Tyr-Pro-Gly-Arg-Phe-Glu-Thr-Ala-Val-Val-Glu-Asp-Met-Leu-Lys-Gln-Gly-

Ala-Tyr-Asp-Glu-Val-Ile-Lys-Gly-Ala-Ala-Gly-Val-Ala-His-Ile-Ala-Ser-Val-Val-

Ser-Phe-Ser-Asn-Lys-Tyr-Asp-Glu-Val-Val-Thr-Pro-Ala-Ile-Gly-Gly-Thr-Leu-Asn-

Ala-Leu-Arg-Ala-Ala-Ala-Ala-Thr-Pro-Ser-Val-Lys-Arg-Phe-Val-Leu-Thr-Ser-Ser-

Thr-Val-Ser-Ala-Leu-Ile-Pro-Lys-Pro-Asn-Val-Glu-Gly-Ile-Tyr-Leu-Asp-Glu-Lys-

Ser-Trp-Asn-Leu-Glu-Ser-Ile-Asp-Lys-Ala-Lys-Thr-Leu-Pro-Glu-Ser-Asp-Pro-Gln-

Lys-Ser-Leu-Trp-Val-Tyr-Ala-Ala-Ser-Lys-Thr-Glu-Ala-Glu-Leu-Ala-Ala-Trp-Lys-

Phe-Met-Asp-Glu-Asn-Lys-Pro-His-Phe-Thr-Leu-Asn-Ala-Val-Leu-Pro-Asn-Tyr-Thr-

Ile-Gly-Thr-Ile-Phe-Asp-Pro-Glu-Thr-Gln-Ser-Gly-Ser-Thr-Ser-Gly-Trp-Met-Met-

Ser-Leu-Phe-Asn-Gly-Glu-Val-Ser-Pro-Ala-Leu-Ala-Leu-Met-Pro-Pro-Gln-Tyr-Tyr-

Val-Ser-Ala-Val-Asp-Ile-Gly-Leu-Leu-His-Leu-Gly-Cys-Leu-Val-Leu-Pro-Gln-Ile-

Glu-Arg-Arg-Arg-Val-Tyr-Gly-Thr-Ala-Gly-Thr-Phe-Asp-Trp-Asn-Thr-Val-Leu-Ala-

Thr-Phe-Arg-Lys-Leu-Tyr-Pro-Ser-Lys-Thr-Phe-Pro-Ala-Asp-Phe-Pro-Asp-Gln-Ser-

Gln-Asp-Leu-Ser-Lys-Phe-Asp-Thr-Ala-Pro-Ser-Leu-Glu-Ile-Leu-Lys-Ser-Leu-Gly-

Arg-Pro-Gly-Trp-Arg-Ser-Ile-Glu-Glu-Ser-Ile-Lys-Asp-Leu-Val-Gly-Ser-Glu-Thr-

Ala,
``` is known as *Sporobolomyces salmonicolor* aldehyde reductase II, and is described in Kita et al., *Applied and Environmental Microbiology*, December 1999, p. 5207–5211.

In the reduction process, NADP, an NADP/NADPH cofactor recycling system having a hydride source, such as glucose, and a catalyst, such as glucose dehydrogenase, and an appropriate buffer suitable for maintaining a pH environment of between about 5 and about 10 are used.

In a preferred embodiment of the process, the reduction is conducted at a temperature of between about 25 and about 40° C.

In a more preferred embodiment of the process, the amount of ketoreductase is between about 0.1 and about 10 g/L, and the amount of NADP is between about 0.1 and about 10 g/L.

In a more preferred embodiment of the process, the hydride source is glucose and the catalyst is glucose dehydrogenase.

Specific examples of $R^2$ suitable for the process include

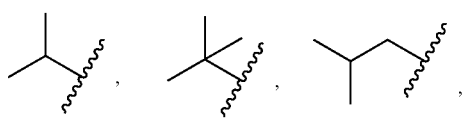

-continued

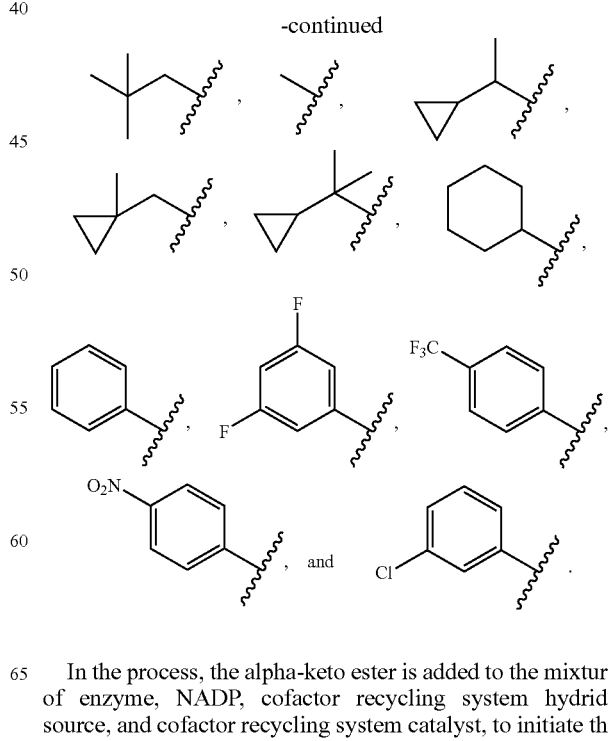

In the process, the alpha-keto ester is added to the mixture of enzyme, NADP, cofactor recycling system hydride source, and cofactor recycling system catalyst, to initiate the reaction. Examples of alpha-keto ester starting materials include ethyl 3-methyl-2-oxobutyrate (Fluka), ethyl benzoylformate (Aldrich), ethyl 3,5-difluorobenzoylformate (Aldrich), ethyl 2-(4-trifluoromethyl)-benzoylformate (Maybridge) and ethyl 4-nitrobenzoylformate (Lancaster). The mixture is maintained at a temperature between about 25 and about 40° C. and agitated appropriately with attention toward providing adequate mixing of buffer and ester oil layer without inducing excessive aeration. Upon completion of the reduction reaction, e.g. about 5 hours, the (R)-hydroxy ester (II) may then be hydrolyzed, e.g. using sodium hydroxide, to form (R)-hydroxy acid (III), according to the procedure

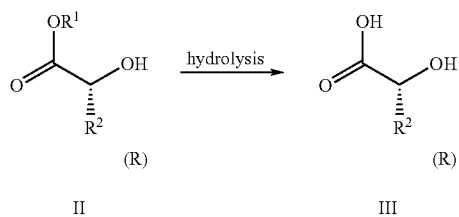

The acid may then be extracted, using a suitable organic solvent, purified, using an appropriate purification procedure, and subsequently used in a process for making a therapeutically active ingredient such as a thrombin inhibitor.

"Cofactor recycling systems" suitable for the present invention regenerate NADPH and include systems in which the hydride source is glucose, glucose-6-phosphate, ethanol, hydrogen gas, or formate, the corresponding catalyst is glucose dehydrogenase, glucose-6-phosphate dehydrogenase, NADP dependent alcohol dehydrogenase, NADP reducing hydrogenase (methyl viologen mediated) or a variant of formate dehydrogenase which accepts NADP.

Alternatively, using a suitable alcohol substrate, the ketoreductase enzyme used in the present process for ketone reduction can be used to convert the alcohol substrate backwards to the ketone, simultaneously generating NADPH. The suitable alcohol substrates include those corresponding to ketones ethyl 3-hydroxybutanoate, ethyl 3-hydroxy-4-chlorobutanoate, and ethyl 3-hydroxy-4-phenylbutanoate, as well as 4-nitrobenzyl alcohol (to form 4-nitrobenzyl aldehyde) and pyridine-3-methanol (to form pyridine-3-aldehyde). The formed ketone or aldehyde is selectively removed, e.g., by evaporation, extraction, or reacting away, for complete conversion to the desired alcohol.

The amount of hydride required in the process depends on whether the cofactor recycling system includes reversible or irreversible steps. For example, if the cofactor recycling system includes an irreversible step (glucose as the hydride source ireversibly converts to gluconate and recycled cofactor) the hydride source is required only in slight molar excess as compared to the keto ester. If the cofactor recycling system does not have an irreversible step, the hydride source may need to be in significant molar excess, or an alternative method for recovering in situ product would be required to bring the reaction to completion.

Alternatively, in the absence of a cofactor recycling system, high concentrations of NADPH may be used directly.

The "appropriate buffer" may be any suitable buffer with a pKa between 6–9, buffering between 5 and 10. Such buffers include, but are not limited to, inorganic carbonate, phosphate, sulfite and hypochlorite bases, and organic buffers, e.g., 2-[N-Morpholino]ethanesulfonic acid, bis[2-Hydroxyethyl]iminotris[hydroxymethyl]methane, piperazine-N,N'-bis[2-ethanesulfnic acid, 3-[N-Morpholino] propanesulfonic acid, tris[Hydroxymethyl]aminoethane, triethanolamine, N-tris[Hydroxymethyl]methyl-3-aminopropanesulfonic acid, and other common organic buffers listed on page 1873 of the Sigma catalog (e.g., HEPES, MOPS, etc.).

The term "alkyl" is intended to include both branched and straight-chain saturated aliphatic hydrocarbon groups having the specified number of carbon atoms. "Substituted" alkyl groups refer to groups having one or more defined substituents. "$C_{1-4}$ alkyl" refers to alkyl groups having 1, 2, 3, or 4 carbon atoms, e.g. methyl, ethyl, propyl, isopropyl, etc. Likewise, "$C_{1-8}$ alkyl" refers to alkyl groups having 1, 2, 3, 4, 5, 6, 7 or 8 carbon atoms.

The terms "cycloalkyl" and "cyclo$C_{3-7}$alkyl" mean non-aromatic cyclic hydrocarbon groups having the specified number of carbon atoms and are intended to include cyclopropyl, cyclobutyl, cyclopentyl, cyclohexyl and cycloheptyl, and the like.

The term "aryl" as used herein except where noted, represents a stable 6- to 10-membered mono- or bicyclic ring system such as phenyl, or naphthyl, wherein at least one ring is aromatic. Unless otherwise specified, the aryl ring can be unsubstituted or substituted with one or more of —$CF_3$, —CN, $C_{1-4}$ alkyl, hydroxy, $C_{1-4}$ alkoxy, halogen (e.g. F, Cl, Br, or I), —$NO_2$, —$NR^aR^b$, —$SO_2R^a$, $SO_2NR^aR^b$, —$CONR^aR^b$, or $COR^a$, wherein $R^a$ and $R^b$ are independently selected hydrogen and $C_{1-4}$ alkyl.

The term "halogen"-includes F, Cl, Br, and I.

The terms "heterocycle", "heterocyclic", and "heterocyclyl" as used herein except where noted, represent a stable 5- to 7-membered monocyclic- or stable 8- to 11-membered fused bicyclic or stable 11- to 15-membered tricyclic ring system, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Bicyclic unsaturated ring systems include bicyclic ring systems which may be partially unsaturated or fully unsaturated. Partially unsaturated bicyclic ring systems include, for example, cyclopentenopyridinyl, benzodioxan, methylenedioxyphenyl groups. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, tetrazole, thienyl, benzothienyl, thiamorpholinyl, thiamorpholinyl sulfoxide, thiamorpholinyl sulfone, and oxadiazolyl. Morpholino is the same as morpholinyl. Unless otherwise specified, the heterocyclic ring may be unsubstituted or substituted with $C_{1-4}$ alkyl, halogen (e.g. F, Cl, Br and I) or $NH_2$.

The term "substituted," as used herein, means that any one or more hydrogens on an atom in a designated moiety is replaced with a selection from the indicated substituent group, provided that the atom's normal valency is not exceeded, and that the substitution results in a stable compound. When a substituent is an keto (i.e., =O), then 2 hydrogens on the atom are replaced.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

(R)-hydroxy esters resulting from reduction of alpha-keto esters may be used to prepare (R)-hydroxy acid intermediates useful in the preparation of compounds, for example, by linking the carboxyl function of the (R)-hydroxy acid with a suitable nitrogen-containing compound, e.g.,

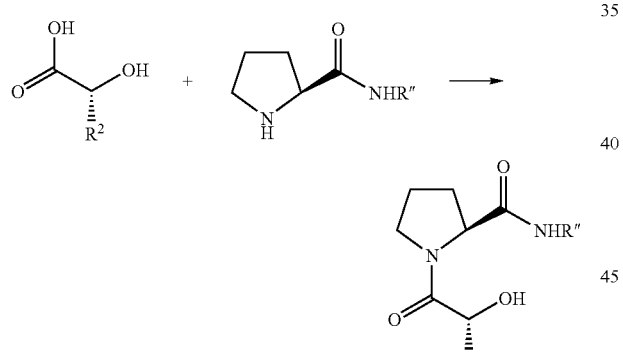

Examples of compounds that can be prepared using the (R)-hydroxy acids described above include those having thrombin inhibiting activity as determined by assays described in Thrombosis Research, Issue No. 70, page 173 (1993) by S. D. Lewis et al., e.g., compounds described in U.S. Pat. Nos. 5,510,369, 5,629,324, 5,672,582, 5,714,485 and 5,798,377.

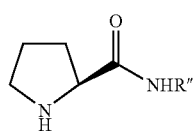

includes, but is not limited to, groups such as

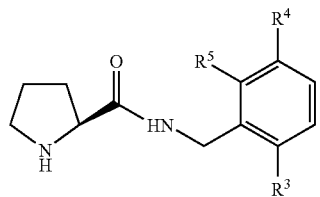

wherein $R^3$ is selected from the group consisting of
1) —$C(R^{11})(R^{12})C(R^{13})(R^{14})N(R^{15})(R^{16})$
2) —$C(R^{13})(R^{14})N(R^{15})(R^{16})$, and
3)

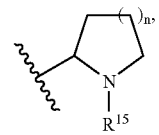

where n is 0, 1 or 2,
wherein
$R^{11}$ and $R^{12}$ are independently selected from the group consisting of
  a) hydrogen,
  b) F,
  c) $C_{1-4}$ alkyl,
  d) $CF_3$,
  e) $CHF_2$,
  f) $C_{3-7}$ cycloalkyl,
    or $R^{11}$ and $R^{12}$ together form a 3–7 membered carbocyclic ring,
$R^{13}$ and $R^{14}$ are independently selected from the group consisting of
  a) hydrogen,
  b) $C_{1-4}$ alkyl
  c) —$CF_3$,
  d) —$CHF_2$,
  e) —$CH_2OH$,
  f) $C_{3-6}$ cycloalkyl,
    or $R^{13}$ and $R^{14}$ together form a 3–7 membered carbocyclic ring,
$R^{15}$ and $R^{16}$ are independently selected from the group consisting of
  a) hydrogen,
  b) $C_{1-6}$ alkyl, unsubstituted or substituted with —OH, $C_{3-7}$ cycloalkyl, or $C(O)OR^{19}$, wherein $R^{19}$ is selected from the group consisting of hydrogen and $C_{1-6}$ alkyl,
  c) $C_{3-7}$ cycloalkyl, and
  d) —$C(O)R^{20}$, wherein $R^{20}$ is selected from the group consisting of $C_{1-6}$ alkyl, —$OR^{21}$ and —$NHR^{21}$, and wherein $R^{21}$ is hydrogen, $C_{1-6}$ alkyl or benzyl,
  or $R^{15}$ and $R^{16}$ are joined to form a 4–7 membered heterocyclic ring which is unsubstituted or substituted with hydroxyl or halogen;
$R^4$ is halogen; and
$R^5$ is hydrogen or halogen.

Thrombin inhibitors are useful in anticoagulant therapy for the treatment and prevention of a variety of thrombotic conditions, particularly coronary artery and cerebrovascular disease. Those experienced in this field are readily aware of the circumstances requiring anticoagulant therapy. Thrombin inhibitors are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood. The thrombin inhibitors can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. The compounds can also be administered in intranasal form via topical use of suitable intranasal vehicles, or via transdermal routes, using those forms of transdermal skin patches well known to those of ordinary skill in that art. The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

The following examples are illustrative of the invention but should not be interpreted as limiting the scope of the invention as defined above.

EXAMPLE 1

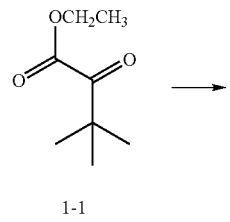

1-1

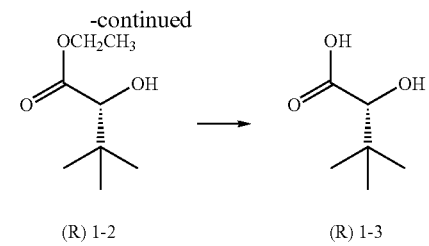

(R) 1-2                     (R) 1-3

6.4 L of a 200 mM $K_2HPO_4$ buffer (544.64 grams in 10 L of Millipore water), 448 grams of glucose, 3.2 grams of glucose dehydrogenase, 0.736 grams of NADP, 0.64 grams of KRED 1001 (Biocatalytics, Inc., Pasadena, Calif.) ketoreductase enzyme, were added to a mixing vessel in order to form a mixture. 295.2 grams of ethyl trimethylpyruvate $((CH_3)_3C(O)C(O)OCH_2CH_3)$ 1-1 was added to the mixture to form a final volume of 6.4 liters. The reaction was allowed to proceed at 25° C. and 222–223 rpm. The pH was controlled at 7.0 using NaOH (5-20% v/v). The reaction proceeded for 5 hours to form ester (R) 1-2. After bioconversion was completed, concentrated NaOH (50% v/v) was poured into the reaction solution in a 1:10 ratio. The final volume of the reaction (including the addition of 5% NaOH during pH control) was approximately 7.2 L.

EXAMPLE 2

Example 1 is repeated, except that the glucose/glucose dehydrogenase cofactor recycling system is replaced with a glucose-6-phosphate/glucose-6-phosphate dehydrogenase cofactor recycling system, wherein the amount of glucose-6-phosphate hydride source is used in molar amounts in slight excess to molar amounts of the keto ester.

EXAMPLE 3

Example 1 is repeated, except that the glucose/glucose dehydrogenase cofactor recycling system is replaced with an ethanol/NADP dependent alcohol dehydrogenase cofactor recycling system, wherein the amount of ethanol hydride source is used in molar amounts in great excess to molar amounts of the keto ester.

EXAMPLE 4

Example 1 is repeated, except that the reaction proceeds for 10 hours to form ester (R) 1-2.

EXAMPLE 5

Example 1 is repeated, except that the reaction proceeds for 16 hours to form ester (R) 1-2.

What is claimed is:

1. A process for preparing (R)-hydroxy ester (II)

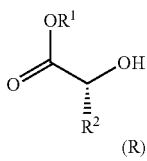

from alpha-keto ester I

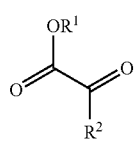

comprising adding the alpha-keto ester I to a mixture comprising a ketoreductase enzyme and non-ketoreductase enzyme components,
wherein
$R^1$ is $C_{1-4}$ alkyl; and
$R^2$ is selected from the group consisting of $C_{1-8}$ alkyl, $C_{1-8}$ alkyl, substituted with $C_{3-7}$ cycloalkyl, aryl, and a 5- to 7-membered saturated or unsaturated heterocyclic ring,
wherein the ketoreductase enzyme has a molecular weight between 36000 and 38000, and wherein the ketoreductase enzyme has an N-terminal amino acid sequence selected from the group of sequences consisting of (SEQ. ID NO. 1)
Ala-Ale-Pro-Asp-Asn-Ala-Val-Leu-Glu-Gly-Ser-Leu-
Val-Lys-Val-Thr-Gly-Ala-Asn-Gly (SEQ. ID NO. 4)
Met-Ala-Ile-Pro-Asp-Asn-Ala-Val-Leu-Glu-Gly-Ser-
Leu-Val-Lys-Val-Thr-Gly-Ala-Asn-Gly, and (SEQ ID NO. 2)
Met-Ala-Lys-Ile-Asp-Asn-Ala-Val-Leu-Pro-Glu-Gly-
Ser-Leu-Val-Leu-Val-Thr-Gly-Ala-Asn-Gly.

2. A process of claim 1, wherein the N-terminal amino acid sequence is selected from the group consisting of (SEQ. ID NO. 1)
Ala-Ile-Pro-Asp-Asn-Ala-Val-Leu-Glu-Gly-Ser-Leu-
Val-Lys-Val-Thr-Gly-Ala-Asn-Gly, and (SEQ. ID NO. 4)
Met-Ala-Ile-Pro-Asp-Asn-Ala-Val-Leu-Glu-Gly-Ser-
Leu-Val-Lys-Val-Thr-Gly-Ala-Asn-Gly.

3. A process of claim 2, wherein the non-ketoreductase enzyme components comprise NADP, a cofactor recycling system comprising a hydride source and a catalyst, and a buffer suitable for maintaining a pH of between about 5 and about 10.

4. A process of claim 3, wherein temperature is between about 25 and about 40° C.

5. A process of claim 4, wherein the hydride source is glucose and the catalyst is glucose dehydrogenase.

6. A process of claim 5, wherein the mixture comprises an amount of ketoreductase between about 0.1 and about 10 g/L, an amount of NADP between about 0.1 and about 10 g/L.
7. A process of claims 1, wherein $R^2$ is selected from the group consisting of
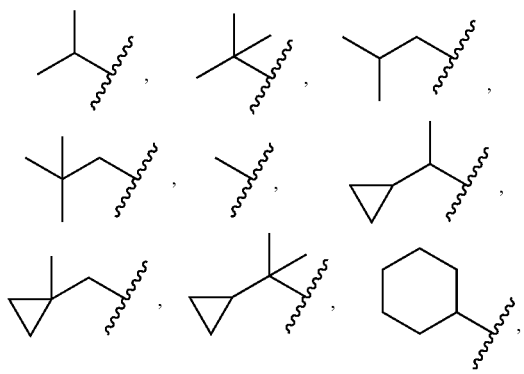
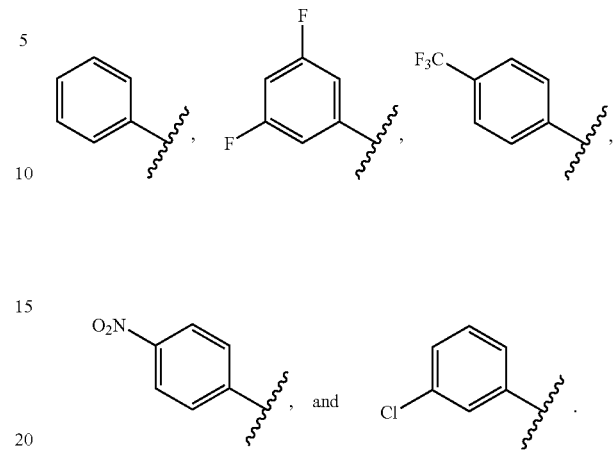
* * * * *